Aug. 13, 1935. A. M. LOWMAN Plant Pat. 130
ROSE
Filed Oct. 10, 1934
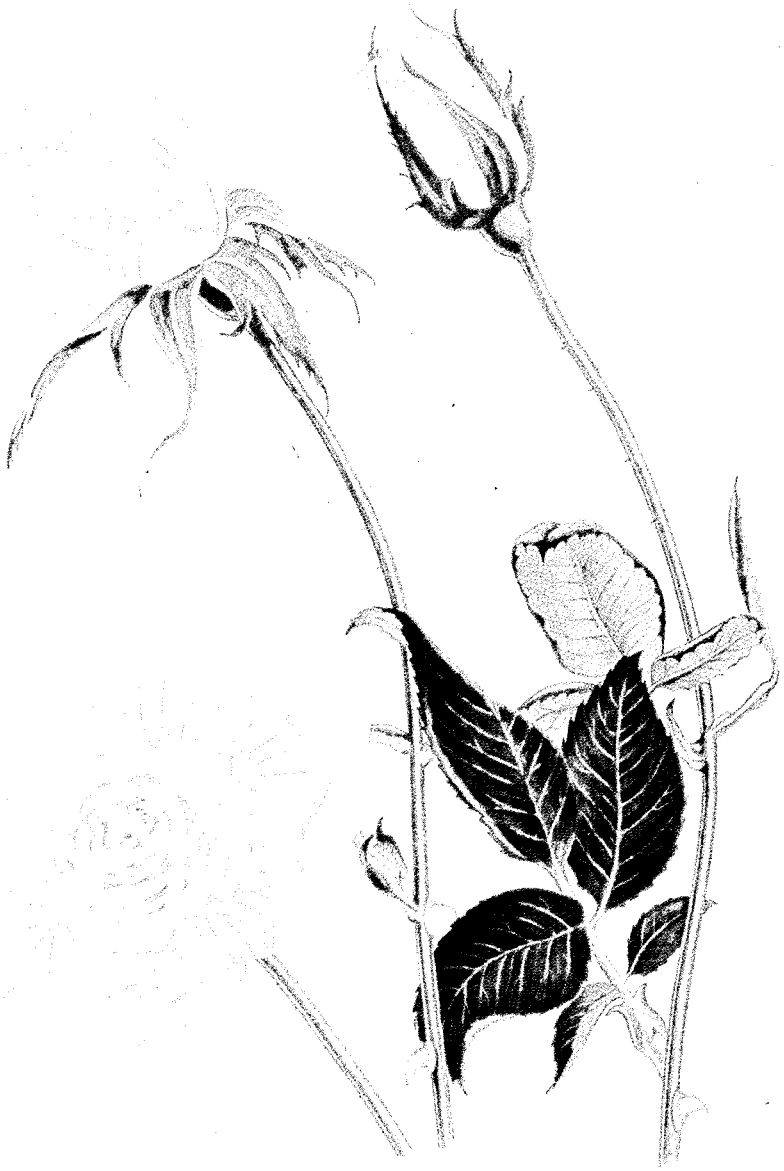
Inventor
Abner M. Lowman.
By Cushman, Darby & Cushman
Attorneys Patented Aug. 13, 1935

Plant Pat. 130

UNITED STATES PATENT OFFICE

130

ROSE

Abner Marshall Lowman, Elmira, N. Y., assignor to United States Cut Flower Co., Elmira, N. Y., a corporation of New York Application October 10, 1934, Serial No. 747,791

1 Claim. (Cl. 47—61)

The present invention relates to a new rose, particularly distinguished by its yellow blooms. The new rose is characterized by vigorous growth, blooming in the hothouse throughout the year and developing marketable cut flowers every six to eight weeks. The pleasing foliage is of distinctive and attractive texture and color. The plant reproduces easily asexually and runs true to type.

In the drawing which forms a part of this specification, the rose is shown in its development from bud to bloom, and the peduncle, foliage, stipules and other parts, indicating the characteristics in form and color of the new type, are illustrated. For the sake of saving space, a group of leaves has been omitted from the central stem, the rachis being shown as severed.

The novel rose of my invention originated as a sport of the Hybrid Tea rose known as Token. The scions of this sport were grafted on the Rosa Manetti root stocks resulting in strong, vigorous plants which during a year's trial have run true to type. Up to the present, no attempt has been made by me to grow the new rose outdoors.

*Plant.*—It is of medium size of strong and vigorous growth and has the valuable tendency to throw new shoots from the base of the plant. It "breaks" very freely with very little blind wood during cloudy winter weather.

*Peduncle.*—The peduncle is of lettuce green color. It has a moderate number of spines or prickles of reddish color and is fully capable of supporting the flower in an upright position at its fullest development.

*Stem.*—The stem is of the same lettuce green color as the peduncle with few well defined downwardly hooked thorns of reddish hue beginning ordinarily below the second or third leaves, the stem being smooth above the latter up to the first leaves. The internodes are comparatively short. The canes are medium in size.

*Foliage.*—The leaves are of medium size and their color is Varley's green according to Ridgeway's Color Standard and Nomenclature (Plate XVIII, Edition of 1912), the general form of the leaflets being flat with the edges curling slightly downwardly and having very fine serrations which are slightly reddish or rust colored. The top surface of the leaflet is glossy and the leaflets are fairly thick and highly resistant to fungus diseases. The rachides ordinarily have a small thorn or two on the underside. The petioles are strong and hold the leaflets straight, the upper side of the petioles having a slightly reddish cast. The stipules are small, lying close to the rachis and ending in sharp points.

Ordinarily, the first leaflets extend from substantially diametrically opposite points of the stem, there being usually a group of three leaflets at one side and a single leaflet at the other side although there may be two groups of three leaflets each. The lower leaflets are ordinarily in groups of five.

*Hips.*—The hips are fairly heavy and taper down to the peduncle in a true urn-shape. The sepals, five in number, have a broad base and are relatively sharply tapered. Two or three of the sepals have plain margins and tips, the others having foliaceous appendages adjacent the base and at the tip.

*Bud.*—The bud, before the calyx breaks, is medium in size and ovoid in form with slightly foliaceous appendages on the surface of the bud but not extending beyond the tip of the latter. The petals are closely nested and afford a bud of firm make-up. As the bud opens, a slight flare develops at the tip.

As the calyx breaks, the color is most intense, the color being the same as that of the flower, to be described hereinafter, except more pronounced or brighter. The bud opens up very well.

*Flowers.*—The flowers or blooms have in general an overall yellowish color ranging from pinard yellow, Ridgeway's Color Standard and Nomenclature (Plate IV, Edition of 1912) for the outside petals to primuline yellow at the center, Ridgeway's Color Standard and Nomenclature (Plate XVI, Edition of 1912) so that the general mass is of pinard yellow blending toward the center into primuline yellow. The color of the inner sides of the base portions of the petals is of particular brightness and the coloring as a whole becomes more pronounced or brighter as the petals are closer to the center. The edges of the outer and larger petals change in full bloom to a naphthalene yellow, Ridgeway's Color Standard and Nomenclature (Plate XVI, Edition of 1912), the main portions of these petals, however, maintaining a true pinard yellow both inside and out. As the blossom ages, faint veins or pencilings of a delicate greenish tint become visible; the petals and sepals persist. Particularly in cloudy winter weather, the outside petals may have areas of a pinkish tinge.

The bloom is full and massive in appearance but at the same time, has a delicacy of shape and coloring which gives it marked distinguishing characteristics, the color tone of the bloom persisting for quite a considerable period without any marked change or discoloration.

The petals of the medium open flower are definitely belled, that is, they are markedly concave at their lower portions so that the blossom stands up firmly. The petals are thick and soft with inside and outside velvety. As the flower develops, the outside petals are mostly round, but some are obovate and some are round except for obtuse apex. The intermediate petals are nearly round but with obtuse apex. Some petaloids or innermost petals are obovate or nearly round with obtuse outwardly projecting apex; others are obovate but with a notch instead of a projecting apex. The bloom never attains a high center.

The blossom is double and of medium size and has a moderate fragrance of a very noticeable Tea character when the flower is half developed.

The stamens are considerable in number and have anthers of uniform size and orange in color, the base of the stamens being yellowish green. The pistils have a reddish cast at the base with whitish stigma. The petals, petaloids, stamens and pistils are in good concentric arrangement, not intermingled.

The average flower has from twenty-four to twenty-seven full petals.

*Habit.*—The plant is of upright growth, free blooming with uniform buds and flowers and is especially adapted for greenhouse culture.

The disclosure herein is particularly directed to a greenhouse plant as in the fall of the year.

The new rose is easily distinguished from roses such as Lady Hillingdon, Ville de Paris, Souvenir de Claudius Pernet, and from Token, the parent, in that the Lady Hillingdon flower is deep apricot-yellow and the foliage bronze-green; in that the Ville de Paris flower is sun-yellow, habitually slightly tinted orange, and the foliage reddish-green; in that the Souvenir de Claudius Pernet flower is sun-flower yellow and the foliage is dark green in color; and in that Token has an orange flower color, although in other respects the new rose closely follows the parent.

Having fully disclosed the invention, I claim:

The variety of rose herein shown and described, characterized particularly by the distinctive yellow color of its flowers, its relative freedom from thorns and spines, its foliage of distinguishing green color, its vigorous growth and free blooming, and its resistance to fungus diseases.

ABNER MARSHALL LOWMAN.